(12) United States Patent
DeSousa et al.

(10) Patent No.: US 6,548,741 B2
(45) Date of Patent: Apr. 15, 2003

(54) DEVELOPMENTAL COMPETENCE FOR ASSISTED REPRODUCTION AND NUCLEAR TRANSFER IN PIGS

(75) Inventors: Paul Alexandre DeSousa, Roslin (GB); Timothy James King, Roslin (GB); Ian Wilmut, Roslin (GB); Jie Zhu, Roslin (GB)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/832,312

(22) Filed: Apr. 9, 2001

(65) Prior Publication Data

US 2001/0049829 A1 Dec. 6, 2001

Related U.S. Application Data

(63) Continuation of application No. PCT/GB99/03384, filed on Oct. 12, 1999.
(60) Provisional application No. 60/104,116, filed on Oct. 13, 1998.

(51) Int. Cl.[7] .................. C12N 15/00; A01K 67/00; A01K 67/027

(52) U.S. Cl. .................. 800/24; 800/8; 800/17

(58) Field of Search .................. 800/3, 18, 21, 800/22, 25, 24, 8, 17; 435/455, 463, 320.1, 325

(56) References Cited

U.S. PATENT DOCUMENTS

| | | | |
|---|---|---|---|
| 5,914,268 A | 6/1999 | Keller et al. | 435/325 |
| 5,942,435 A | 8/1999 | Wheeler | 435/325 |
| 5,994,619 A | 11/1999 | Stice et al. | 800/12 |
| 6,147,276 A | 11/2000 | Campbell et al. | 800/24 |
| 6,252,133 B1 | 6/2001 | Campbell et al. | 800/24 |
| 6,258,998 B1 | 7/2001 | Damiani et al. | 800/24 |

FOREIGN PATENT DOCUMENTS

| | | |
|---|---|---|
| WO | WO 95/28412 | 10/1995 |
| WO | WO/9707668 | * 3/1997 |
| WO | WO 99/01164 | 1/1999 |
| WO | WO 99/46982 | 9/1999 |
| WO | WO 00/42174 | 7/2000 |

OTHER PUBLICATIONS

Wang et.al.; Naturation and Fertilization of Porcine Oocytes in Vitrop, 1992, Theriogenology 37: 733–739.*
Funahashi et.al.; In Vitro Development of in Invitro–Matured Porcine OOcytes Following Chemical Activation or in Vitro Fertilization, 1994, Biology of Reproduction 50: 1072–1077.*
De Sousa et al., Somatic cell nuclear tranfer in the pig: control of Pronuclear formation and integration with improved methods for activation and maintenance of pregnancy, Galley proof (not yet published; to appear in Biol Reprod).
Betthauser et al., Production of cloned pigs from in vitro systems, Nat Biotechnol 18:1055 (2000).
Onishi et al., Pig cloning by microinjection of fetal fibroblast nuclei, Science 289:1185 (2000).
Betthauser, et al., Production of Cloned Pigs from Vitro Systems, Nature Biol. 18:1055 (2000).
Boland, et al., Embryo Production: Alternatie Methods, Mol. Reprod. Dev. 36:266 (1993).
Campbell, et al., Improved Development to Blastocyst of Ovine Nuclear Transfer Embryos Reconstructed During the Presumptive S–Phase of Enucleated Activated Oocytes, Biol. Reprod. 50:1385 (1994).
Campbell, et al., Sheep Cloned by Nuclear Transfer From a Cultured Cell Line, Nature 380:64 (1996).
Cibelli, et al., Cloned Transgenic Calves Produced From Nonquiescent Fetal Fibroblasts, Science 280:1256 (1998).
De Sousa, et al., Temporal Patterns of Embryonic Gene Expression and Their Dependence on Oogenetic Factors, Theriogenology 49:115 (1998).
De Sousa, et al., Evaluation of Gestational Deficiencies in Cloned Sheep Fetuses and Placentae, Biol. Reprod. 65:23 (2001).
Driancourt, et al., Follicular gtowth nd maturation in hyper-prolific and large white sows, J Anim Sci 74:2231 (1996).
Draincourt, Regulation of ovarian follicular dynamics in farm animals. Implications for manipulation of reproduction., Theriogenology 55:1211 (2001).
Dzuik, et al., Effect of Migration, Distribution and Spacing of Pig Embryos on Pregnancy and Fetal Survival, J. Reprod. Fert., Supp. 33:57 (1985).
Funahashi, et al., Advances in In Vitro Production of Pig Embryos, J. Reprod. Fert. Suppl. 52:271 (1997).
Funahashi, et al., Synchronization of Meiosis in Porcine Oocytes by Exposure to Dibutyryl Cyclic Adenosine Monophosphate Improves Developmental Competence Following In Vitro Fertilization, Biol. Repro. 57:49 (1997).

(List continued on next page.)

Primary Examiner—Deborah Crouch
Assistant Examiner—Thaian N. Ton
(74) Attorney, Agent, or Firm—J. Michael Schiff; David J. Earp

(57) ABSTRACT

An optimum time has been discovered for obtaining porcine oocytes with improved developmental competence. Harvested oocytes are matured by culturing in vitro, and then activated ~42–46 hours after beginning of the culture period. Alternatively, ovulation is induced in a donor female using a gonadotrophic hormone (optionally monitored by ultrasonography), maturation is allowed to proceed in vivo, and then the harvested oocyte is activated ~44–48 hours after inducing ovulation. Outside the optimal time frame, the ability of the oocytes to undergo parthenogenetic activation declines markedly. These methods overcome problems encountered with previous protocols for nuclear transfer and assisted reproduction in the pig.

10 Claims, 4 Drawing Sheets

OTHER PUBLICATIONS

Grupen, et al., Role of Epidermal Growth Factor and Insulin–like Growth Factor–I on Porcine Oocyte Maturation and Embryonic Development In Vitro, Reprod. Fert. Dev. 9:571 (1997).

Grupen, et al., Activiation of In Vivo– and In Vitro–Derived Porcine Oocytes by Using Multiple Electrical Pulses, Reprod. Fertil. Dev. 11:457 (1999).

Joliff, et al., Parthenogenic Development of In Vitro–Matured, In Vivo–Cultured Porcine Oocytes Beyond Blastocyst, Biol. Reprod. 56:544 (1997).

Kikuchi, et al., Developmental Competence, After Transfer to Recipients, of Porcine Oocytes Matured, Fertilized and Cultured In Vitro, Biol. Reprod. 60:336 (1999).

Koo, et al., Developmental Potential and Transgene Expression of Porcine Nuclear Transfer Embryos Using Somatic Cells, Mol. Reprod. Dev. 58:15 (2001).

Liu, et al., Nuclear Remodeling and Early Development in Cryopreserved, Porcine Primordial Germ Cells Following Nuclear Transfer Into In Vitro–Matured Oocytes, In. J. Dev. Biol. 39:639 (1995).

Liu, et al., Role of Secreted Proteins and Gonadotrophins in Promoting Full Maturation of Procine Oocytes In Vitro, Mol. Reprod. Dev. 47:191 (1997).

Liu, et al., Factors Affecting Electrical Activation of Porcine Oocyte Matured In Vitro, Anim. Reprod. Sci. 48:67 (1997).

Machaty, et al., Parthenogenetic Activation of Porcine Oocytes with Guanosine–5'–0–(3'–thiotriphosphate), Biol. Reprod. 52:753 (1995).

Moor, et al., Effect of Follicular Steroids on the Maturation and Fertilization of Mammalian Oocytes, JEEM 56:319 (1980).

Nagashima, et al., Nuclear transfer of Porcine Embryos Using Cryopreserved Delipated Blastomeres as Donor Nuclei, Mol. Reprod. Dev. 48:339 (1997).

Nottle, et al., Developments in Transgenic Techniques in Pigs, J. Reprod. Fert. Supp. 52:237 (1997).

Onishi, et al., Pig Cloning by Microinjection of Fetal Fibroblast Nuclei, Science 289:118 (2000).

Pavlok, et al., Transcriptinal Activity and Nuclear Ultrastructure of 8–Cell Bovine Embryos Developed by In Vitro Maturation and Fertilization of Oocytes From Different Growth Catagories of Antral Follicles, Mol. Reprod. Dev. 35:233 (1993).

Pinkert, et al., In Vitro Development of Zygotes from Superovulated Prepubertal and Mature Gilts, J. Reprod. Fert. 87:63 (1989).

Prather, et al., Arificial Activation of Porcine Oocytes Matured In Vitro, Mol. Reprod. Der. 28:405 (1991).

Polejaeva, et al., Cloned Pigs Produced by Nuclear Transfer from Adult Somatic Cells, Nature 407:86 (2000).

Polge, et al., The Effect of Reducing the Number of Embryos During Early Stages of Gestation on the Maintenance of Pregnancy in the Pig, J. Reprod. Fert. 12:395 (1966).

Soede, et al., Ultrasonography of Pig Ovaries: Benefits in Research and on Farms, Reprod. Dom. Animals 29:366 (1994).

Soede & Kemp, Consequences of Variation in Interval from Insemination to Ovulation on Fertilization in Pigs, J. Reprod. Fert. Suppl. 52:79 (1997).

Soede & Kemp, Expression of Oestrus and Timing of Ovulation in Pigs, J. Reprod. Fert. Suppl. 52:91 (1997).

Verma, et al., In Vitro Development of Porcine Nuclear Transfer Embryos Constructed Using Fetal Fibroblasts, Mol. Reprod. Dev. 57:262 (2000).

Wilmut, et al., Viable Offspring Derived From Fetal and Adult Mammalian Cells, Nature 385:810 (1997).

* cited by examiner

OVULATION TIMES

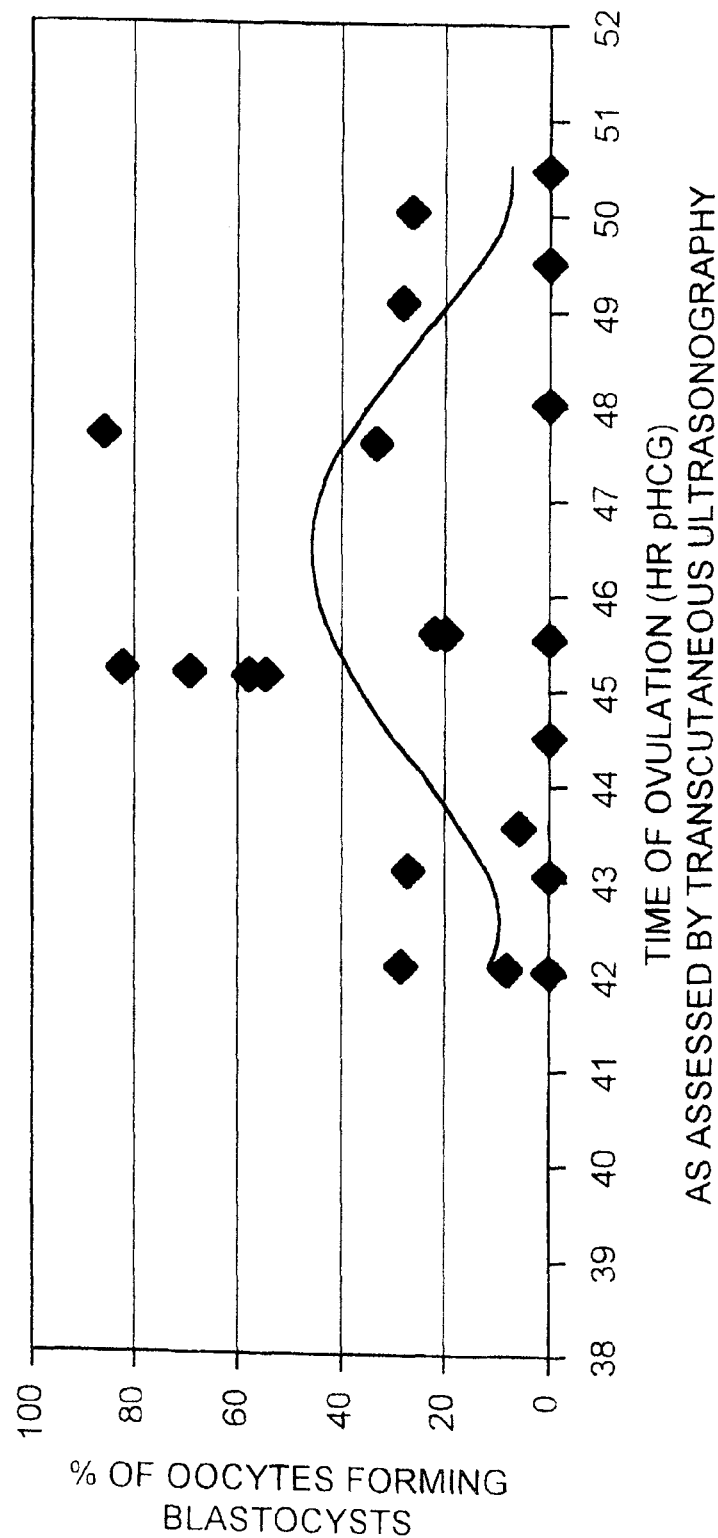

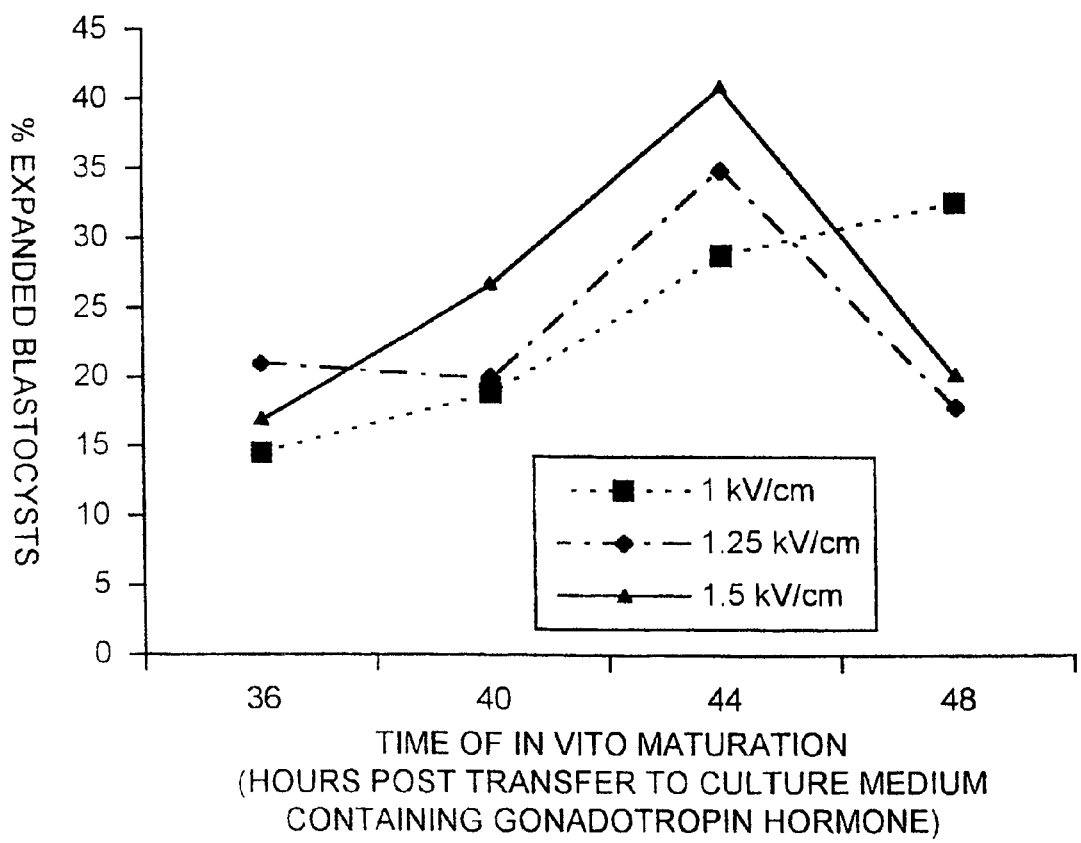

DEVELOPMENTAL COMPETENCE FOR ASSISTED REPRODUCTION AND NUCLEAR TRANSFER IN PIGS

REFERENCE TO RELATED APPLICATIONS

This application is a continuation of International Application PCT/GB99/03384, filed Oct. 12, 1999, designating the United States. The PCT application and the current application claim the priority benefit of United Kingdom application GB 9822235.9, filed Oct. 12, 1998; and U.S. provisional application No. 60/104,116, filed Oct. 13, 1998.

FIELD OF THE INVENTION

This invention relates to the harvesting of porcine oocytes with improved developmental competence and to the generation of pigs by assisted reproduction strategies, including nuclear transfer including but not being limited to, genetically selected and/or modified animals.

BACKGROUND OF THE INVENTION

The female reproductive cycle begins with maturation and ovulation of the oocyte within the female reproductive tract. In normal sexual reproduction, fertilization of the oocyte by sperm also occurs in the reproductive tract. Assisted reproduction strategies, such as in vitro fertilization (IVF) and nuclear transfer, use oocytes that are harvested from the female animal at some point prior to fertilization and subsequently processed in vitro. Since the fertile life span of an oocyte is short, defining the optimal period within which to retrieve oocytes for reproductive strategies is invaluable, as is insight into how that period can be manipulated. Currently, assisted reproduction strategies use oocytes that are selected at random from a matured oocyte population. Typically, such oocyte populations are removed from the ovaries of slaughterhouse animals and matured in vitro, or are harvested from superovulated pigs and are thus matured in vivo.

There is little known of the factors that define the competence of an animal oocyte to develop following ovulation and/or maturation. Although developmental competence is positively correlated with the size of the follicles from which they are derived (Pavlok et al., *Mol. Reprod. Dev.* 35 233–243 (1993)), not all large follicles ovulate and in fact most undergo atresia, with concomitant loss of the oocyte within (Driancourt, *Theriogen* 35 55–79 (1991)). A more likely factor is the requirement for a specific follicular steroid environment (Moor et al., *JEEM* 56 319–335 (1980)). In support of this studies in cattle and sheep have demonstrated follicular differences in growth and steroid hormone expression correlated with dominant and secondary waves of folliculogenesis (reviewed by Roche *Rev of Reprod* 1 19–27 (1996)).

To overcome the hurdles imposed by the finite life and undefined characteristics of a developmentally competent oocyte two approaches have been taken. The first approach uses exogenous gonadotropins to induce (super) ovulation, and the second bypasses ovulation and recapitulates the maturation of oocytes in vitro under defined conditions (reviewed in Boland and Roche, *Mol. Reprod. Dev.* 36 266–270 (1993)). Both methods improve the success of reproductive strategies by providing increased numbers of oocytes for subsequent insemination and/or manipulation. However, these methods do not guarantee optimal developmental competence of the oocytes that they provide. Superovulation of prepubertal sheep, pigs, and cattle still results in oocytes of diminished developmental competence compared with oocytes derived from post-pubertal animals (Wright et al., *J. Anim. Sci.* 42 912–917 (1976); Pinkert et al., *J Reprod. Fert.* 87 63–66 (1989); Seidel et al., *Dairy Sci.* 54 923–926 (1971)). In addition, oocytes matured in vitro as cumulus-oocyte-complexes are highly heterogeneous in their morphology and quality. The abundance of cumulus coverage surrounding oocytes has been positively correlated with their developmental competence following in vitro maturation (Leibried-Rutledge and First, *J. Anim. Sci.* 48 76–86 (1979); De Loos et al., *Gamete Res.* 24 197–204 (1989); Blondin and Sirard, *Mol. Reprod. Dev.* 41 54–62 (1995); Funahashi and Day, *J. Reprod. Fert. Suppl.* 52 271–283 (1997)).

Previous studies in the pig have monitored ovulation by either slaughter, laparoscopy, or transcutaneous or transrectal ultrasound (Hunter *Res. Vet. Sci.* 13 356–361 (1972); Brussow et al., *Reprod. in Dom. Anim.* 25 255–260 (1990); Weitze et al., *Reprod. Dom. Anim.* 25 61–67 (1990); Weitze et al *Zuchthyg.* 24 40–42 (1989); Soede et al., *Theriogen* 38 653–666 (1992)). In the pig the timing of ovulation during the oestrus phase of the reproductive cycle is highly variable. For example, in spontaneously ovulating animals, timing may vary from between 10 to 85 hours after the onset of oestrus (reviewed by Soede and Kemp *J. Reprod. Fert. Suppl.* 52 91–103 (1997)). This can be shortened by 5 to 14 hours following intracervical infusion of seminal plasma (Weitze et al., *Reprod. Dom. Anim.* 25 61–67 (1990)). Such infusion has no effect on the synchronized ovulatory response of gonadotropin treated gilts (Brussow et al., *Reprod. Dom. Anim.* 28 119–122 (1992)), which ovulate between 35 to 50 hours post stimulation depending on the gonadotropin used (reviewed by Kemp and Soede, *J. Reprod. Fertil. Suppl.* 52 79–89 (1997)).

Seasonally reduced fertility in pigs, known as "summer infertility", has been reported, although this effect is less pronounced than in wild pigs or other species such as the sheep (reviewed by Claus and Weiler *J. Reprod. Fert. Suppl.* 33 185–197 (1985)). In sheep, variations in the duration of day length have been demonstrated as the regulatory stimulus controlling the pattern of seasonal reproduction. Effects of photoperiod are transduced from neuronal to endocrine signals by the stimulation of the pineal gland, which produces hormones such as melatonin that in turn stimulate gonadotropin release. Diurnal variations in porcine plasma melatonin have been described (Klupiec et al., *J. Pineal Res.* 22 65–74 (1997)). However, there is no evidence that melatonin or its precursors and metabolites are involved in regulating ovulation or reproductive performance (Foxcroft et al., in "Principles of pig science", ed. DJA Cole, Nottingham University Press (1994)).

In general the mechanisms establishing ovulation rate in the pig are poorly understood. In the pig, growth and development of a follicle is dependent on pituitary gonadotropins from the time it acquires theca interna cells. The growth of selected preovulatory follicles in the pig is also associated with rapid atresia of smaller follicles (Foxcroft and Hunter, *J. Reprod. Fertil. Suppl.* 33 1–19 (1985)). This is consistent with the existence of a dominant follicular wave suggested for monotocous species such as cattle. Recruitment of follicles from the antral follicle pool (and thus rescue from atresia) is also known to be induced by a specific pattern of episodic Lutenizing hormone release (reviewed by Kemp et al., "Control of Ovulation" in "Progress in Pig Science", ed. Wisemean, Nottingham University Press (1988)).

A limited number of studies have attempted to examine the relationship between embryonic survivability and either the duration of ovulation or its early induction in the pig. Initial reports suggested that the first ovulating follicles resulted in the best developing embryos in a litter (Pope et al., *Biol. of Reprod.* 39 822–887 (1988); Xie et al., *Biol. of Reprod.* 43 236–240 (1990)). However, these results have been challenged by others (Soede et al., *Theriogen* 38 653–666 (1992); Soede and Kemp *Theriogen* 39 1043–1053 (1993)). Early embryonic survivability has also been found to be unaffected by early induction of ovulation, induced by varying the timing of gonadotropin injections relative to each other (reviewed by Kemp et al., "Control of Ovulation" in "Progress in Pig Science", ed. Wisemean, Nottingham University Press (1988)). There have been no reports suggesting improved embryonic survivability following delayed ovulation of the oocyte used to prepare the embryo. A single study has described the collection of porcine oocytes at later time points relative to injection of gonadotropin in which the oocytes are said to show an improved capacity to be activated and develop to the blastocyst stage following nuclear transfer. However, in this study the timing of ovulation was not recorded and nor was the stage in the diurnal cycle of the animal noted. The beneficial effect was attributed by the authors to ageing of the oocytes within the oviduct (Nagashima et al., *Mol. Reprod. Dev.* 48 339–343 (1997)).

It is known that ovulation in pigs occurs over a broad time range (observed to be 10–85 hours post-oestrus) under normal conditions where oocytes ovulate spontaneously. More controlled ovulation has been obtained using superovulation protocols where ovulation is generally seen 35–50 hours post-injection with a gonadotropin hormone to induce ovulation. However, it is difficult to obtain oocytes of sufficiently high quality from either route for use in assisted reproduction, including nuclear transfer, even with the introduction of superovulation protocols. In assisted reproduction strategies such as in vitro fertilization (IVF) and nuclear transfer there is therefore a need to improve the efficiency of the process by selecting the best possible oocytes from a matured population of oocytes.

SUMMARY OF THE INVENTION

An optimum time frame or "window" of developmental competence for porcine oocytes as measured by parthenogenetic activation of the oocytes has now been discovered. The optimum time frame or window has been demonstrated in oocytes obtained by both in vivo and in vitro maturation. The invention provides methods for selecting oocytes having maximal developmental competence which can be suitably measured by parthenogenetic activation of oocytes prepared according to a method of the invention. Parthenogenetic activation is a convenient method by which the developmental competence of oocytes can be measured. It is generally considered to accurately reflect the competence of oocytes to develop when used in nuclear transfer or in IVF protocols.

Outside of this window of developmental competence now discovered, the ability of porcine oocytes to undergo parthenogenetic activation declines markedly, i.e. the oocytes are less capable of development in assisted reproduction strategies. In unselected populations of oocytes there will be a large proportion of cells that are outside of the window.

According to a first aspect of the invention there is provided a method of producing a porcine oocyte optimised for developmental competence, the method comprising culturing a harvested oocyte in vitro for between about 36 to about 48 hours. Methods in accordance with this aspect of the present invention also extend to selection of a population of porcine oocytes with improved developmental competence.

According to a second aspect of the invention there is provided a method of producing a porcine oocyte optimised for developmental competence, the method comprising harvesting an oocyte from a pig from about 42 to about 50 hours post-injection with a gonadotropin hormone, wherein the oocyte was ovulated from about 42 to 50 hours post-gonadotropin injection. Methods in accordance with this aspect of the present invention also extend to selection of a population of porcine oocytes with improved developmental competence. Detection of ovulation in the pig can conveniently be monitored using transcutaneous ultrasonography.

Methods in accordance with the second aspect of the invention can conveniently be carried out by delaying the time of ovulation in the donor female animal or by manipulating the fertility cycle of the pig by administering progesterone or an analogue thereof in the middle of the cycle (mid-luteal administration) to the animal. Where mid-luteal administration of progesterone or an analogue thereof is to be employed, the animal to be treated is first monitored to establish the course of its estrous cycle. Once an actively cycling animal is identified, the animal is fed progesterone or an analogue thereof for 4–5 days (at around day 11–15 of the cycle) to maintain anestrous (i.e. mid-luteal administration). Once the hormone supplement is removed, the animal reinitiates another cycle. Injection with a gonadotropin hormone 1 and 4 days later results in ovulation in a controlled manner. This represents an improvement over traditional superovulation protocols which involve progesterone treatment for a full 18 days of the estrous cycle.

A previously unreported and alternative method of delaying ovulation is also encompassed by the invention. As part of experiments aimed at optimizing the timing of the superovulatory response of mature gilts to exogenous gonadotropins, it has now been discovered that the timing of ovulation can be delayed by approximately 3 hours relative to the time of the last gonadotropin injection, without affecting the yield of oocytes. This can be achieved by administering the gonadotropin to the animal by any convenient route, for example by injection, i.e. intravenous, intramuscular, intraperitoneal, subcutaneous, or by other means such as oral, topical, etc. Using transcutaneous ultrasonography to precisely monitor ovulation, oocytes can be retrieved from oviducts following ovulation, and activated to initiate their early developmental program. This alternative method according to the present invention has been found to provide oocytes which have an improved developmental competence. The shift in the time of administration of the gonadotropin hormone in the diurnal rhythm of the animal has been shown to shift the time of ovulation such that in the in vivo maturation period is increased to bring the time of ovulation within the time period or window of optimal developmental competence. The developmental competence of such oocytes to form the end stages of preimplantation development is positively correlated with increased time to ovulation.

Preferred methods in accordance with either the first or the second aspects of the invention are as follows. In an in vitro maturation method of producing a porcine oocyte optimised for developmental competence, the method may comprise: (i) harvesting a cumulus oocyte complex (COC) from a follicle of a pig ovary; and (ii) maturing said COC in a physiologically acceptable culture medium comprising a gonadotropin hormone for between about 36 to about 48 hours. In embodiments where even greater enhanced developmental competence is required, the oocyte or COC may be matured in in vitro for about 42 to about 46 hours or about 43 hours to about 45 hours.

In an in vivo method of producing a porcine oocyte optimised for developmental competence, the method may comprise: (i) injecting an animal with a gonadotropin hormone; and (ii) harvesting an oocyte from a pig from about 42 to about 50 hours post-injection with gonadotropin, wherein the oocyte was ovulated from about 42 hours to about 50 hours as determined by transcutaneous ultrasonography. In embodiments where even greater enhanced developmental competence is required, the oocyte may be harvested from about 44 hours to about 48 hours, wherein the oocyte was ovulated from about 44 hours to about 48 hours as determined by transcutaneous ultrasonography, or alternatively, the oocyte may be harvested from about 45 hours to about 47 hours, wherein the oocyte was ovulated from about 45 hours to about 47 hours as determined by transcutaneous ultrasonography. Ovulation may be seen to occur within about 1 hour to about 6 hours following gonadotropin injection.

Further more specific in vivo methods of producing a porcine oocyte optimised for developmental competence may be as follows. Firstly, the method may comprise: (i) administering progesterone or an analogue thereof to a pig for 18 days to establish a reference heat in the animal; (ii) thirteen to sixteen days subsequently administering to the animal a first injection of Pregnant Mares Serum Gonadotropin (PMSG); (iii) after a time period of 88 hours administering to the animal a second injection of human chorionic gonadotropin (hCG); and (iv) harvesting an oocyte from a pig from about 45 to about 47 hours post-injection with hCG, wherein the oocyte was ovulated from about 45 to 47 hours post-hCG injection as determined by transcutaneous ultrasonography. As an alternative to a method as described above where the hCG injection can be optimally shifted in the diurnal rhythm of the animal such that it takes place 88 hours after the PMSG injection, a preferred method can comprise: (i) administering to the animal progesterone or an analogue thereof for four or five days at days 11 to 15 of the estrous cycle; (ii) subsequently administering to the animal PMSG one day later and hCG four days later to cause ovulation of an oocyte; and (iii) harvesting an oocyte from a pig from about 45 to about 47 hours post-injection with hCG, wherein the oocyte was ovulated from about 45 to 47 hours post-hCG injection as determined by transcutaneous ultrasonography.

Methods in accordance with these aspects of the present invention therefore permit the selection of pig oocytes with an optimised developmental competence in a defined time period. Such oocytes have an increased ability to undergo development following activation. The methods overcome the problems encountered with the previous protocols for porcine oocytes in nuclear transfer and assisted reproduction.

According to a third aspect of the present invention there is provided a method of harvesting an oocyte from a porcine mammal in response to the administration of a gonadotropin hormone, the method comprising administration of the gonadotropin hormone towards the end of the diurnal rhythm of the porcine mammal, and subsequently harvesting the ovulated oocyte.

This aspect of the present invention provides a process by which ovulation in porcine mammals, can be delayed to prolong the residence time of an oocyte within a follicle but where ovulation still occurs at a predictable time so that viable, developmentally competent oocytes may be retrieved within a defined window of time. Methods in accordance with this aspect of the present invention can also be used to enhance the precision of existing protocols to manipulate the timing of ovulation and the quality of the oocytes that are subsequently obtained for natural and assisted reproductive strategies. A major advantage of this aspect of the invention is that it permits the efficacy of these strategies to be increased by increasing the precision with which oocytes are ovulated and handled and improving the likelihood that the oocytes retrieved have a high developmental capacity.

This aspect of the present invention also extends to a method of enhancing the developmental competence of a harvested porcine oocyte, the method comprising administration of a gonadotropin hormone to a porcine mammal towards the end of the diurnal rhythm of the animal prior to harvesting the oocyte such that ovulation is delayed.

According to a fourth aspect of the invention there is provided a method of nuclear transfer, the method comprising the introduction of a nucleus from a donor cell into a porcine oocyte produced in accordance with the first or second aspects of the present invention described above.

According to a fifth aspect of the invention there is provided a method of in vitro production of a porcine embryo, the method comprising the step of in vitro fertilization (IVF) of an oocyte prepared in accordance with the preceding aspects of the invention.

The present invention also extends to an oocyte prepared according to a method as described above. According to a sixth aspect of the invention there is provided a composition of porcine oocytes selected for optimal developmental competence, wherein the oocytes substantially comprise oocytes matured in vitro for between about 36 to about 48 hours. In embodiments of the invention where even greater enhanced developmental competence is desired, the oocytes may be matured for between about 42 to about 46 hours or alternatively for between about 43 to about 45 hours.

According to a seventh aspect of the invention there is provided a composition of porcine oocytes selected for optimal developmental competence, wherein the oocytes substantially comprise oocytes harvested from at least one pig from about 42 to about 50 hours post-injection with a gonadotropin hormone, wherein the oocyte was ovulated from about 42 to about 50 hours post-gonadotropin injection. In embodiments of the invention where even greater enhanced developmental competence is desired, the oocytes may be harvested from the pig from about 44 to about 48 hours post-injection with a gonadotropin hormone, wherein the oocytes were ovulated from about 44 to about 48 hours post-gonadotropin injection. The oocytes can also be harvested from the pig from about 45 to about 47 hours post-injection with a gonadotropin hormone, wherein the oocytes were ovulated from about 45 to about 47 hours post-gonadotropin injection. As in previous aspects of the invention, ovulation of the oocytes may be conveniently detected using transcutaneous ultrasonography.

Also included is the use of separate first and second administrations of gonadotropin hormone to harvest an oocyte from a porcine mammal in which the first administration of gonadotropin hormone is towards the end of the diurnal rhythm of the animal. The gonadotropin hormone may also be used in the manufacture of an agent for the harvesting of an oocyte from a porcine mammal whereby the gonadotropin hormone is administered towards the end of the diurnal rhythm of the animal. This aspect of the invention also extends a kit comprising a gonadotropin hormone wherein the kit contains instructions for administration of the gonadotropin hormone to a porcine mammal for harvesting an oocyte from the animal in which administration of the hormone is towards the end of the diurnal rhythm of the animal. Alternatively, the kit may comprise a first gonadotropin hormone and a second gonadotropin hormone wherein the kit contains instructions for administration of the gonadotropin hormones to a porcine mammal for harvesting an oocyte from the animal in which administration of the first hormone is towards the end of the diurnal rhythm of the animal and administration of the second hormone is separated from the first administration by about three days.

DETAILED DESCRIPTION OF THE INVENTION

1. Definitions

Methods of the present invention are applicable to mammals of the species porcus, including pig species such as Large White, Landrace, Meishan, Minipig. The term "porcine" as used herein refers to any pig species.

The term "oocyte" is used to describe the mature animal ovum which is the final product of oogenesis and also the precursor forms being the oogonium, the primary oocyte and the secondary oocyte respectively. Methods in accordance with the invention may also find application to oocytes collected from transgenic or genetically modified porcine mammals, including chimeras and also oocytes obtained from animals derived from embryos prepared by nuclear transfer procedures. The collection of oocytes from animals for in vitro maturation involves the aspiration of cumulus oocyte complexes (COCs) from the follicles of animals. References to harvesting of oocytes from the follicles of animals prior to in vitro maturation of the oocytes should therefore be understood to include cumulus oocyte complexes.

It should be noted that the term "transgenic", in relation to animals, should not be taken to be limited to referring to animals containing in their genome or germ line one or more genes from another species, although many transgenic animals will contain such a gene or genes. Rather, the term refers more broadly to any animal whose germ line or genome has been the subject of technical intervention by recombinant DNA technology. So, for example, an animal in whose germ line an endogenous gene has been deleted, duplicated, activated or modified is a transgenic animal for the purposes of this invention as much as an animal to whose genome or germ line an exogenous DNA sequence has been added.

In embodiments of the invention in which the animal from which the oocyte is collected is transgenic, the genetic modification to the animal may be undertaken using physical techniques such as microinjection into the male or female pronucleus of the zygote or into the cytoplasm or nucleus of an oocyte or embryo from which the animal develops. Alternatively, the genetic modification can involve the use of mass transformation or transfection techniques such as electroporation, viral transfection (including the use of adenoviruses, retroviruses, adeno-associated means or synthetic retrotransposons), lipofection, microprojectile cell bombardment, antisense technology, vectors such as YAC and BAC or by using other means such as sperm. Furthermore the modification can benefit from intervention by homologous recombination, DNA repair mechanisms, including the use of restriction enzymes. Cell-mediated transgenesis can employ a variety of cells, including ES cells, EG cells and other stem cells or suitable cells from any mammalian species.

Developmental competence is herein defined as the ability of an oocyte to undergo parthenogenetic activation and develop at least to the morula or to the blastocyst stage in terms of embryo development. As discussed above, parthenogenetic activation is seen as a reliable indicator of the ability of an oocyte to develop under normal circumstances following fertilization, such as for example IVF, or following nuclear transfer.

In superovulation protocols, the first step often comprises the administration of progesterone or an analogue thereof to the animal to enable establishment of a reference heat. The progesterone analogue may be, but is not limited to, altrenogest or regumate.

Gonadotropin hormones (gonadotrophins or gonadotropic hormones) are a group of vertebrate glycoprotein hormones, controlling production of specific hormones by gonadal endocrine tissues. Anterior pituitaries of both sexes produce follicle-stimulating hormone (FSH) and lutenizing hormone (LH, or intestitial cell stimulating hormone (ICSH) in males); but their effects in the two sexes are different. Human chorionic gonadotropin (hCG) is an embryonic product whose presence in maternal urine is usually diagnostic of pregnancy. Release of FSH and LH is controlled by hypothalamic gonadotropin-releasing factors (GnRFs), including for example Gonadotropin-releasing hormone (GnRH). Many gonadotropin preparations are known in the art. In methods according to the present invention, the gonadotropin preparation may be, for example, Pregnant Mares Serum Gonadotropin (PMSG), human chorionic gonadotropin (hCG), equine Chorionic Gonadotropin (eCG) or Gonadotropin Releasing Hormone (GnRH). A prostaglandin or synthetic analogue thereof may also be co-administered with the gonadotropin as appropriate. An example of a synthetic prostaglandin hormone is cloprostinol. Other examples are well known in the art.

The administration of the gonadotropin hormones may be undertaken by any generally suitable procedure, including intravenous injection, intramuscular injection, intraperitoneal injection, subcutaneous injection, or by other routes including oral, topical, vaginal, or rectal. Solid dosage or particulate dosage forms may be administered as controlled release formulations where appropriate. Preferably the administration is via an injection.

Ovulation in pigs that have been subjected to a superovulation protocol occurs after injection of the animal with a gonadotropin hormone.

The diurnal rhythm or circadian rhythm of an animal can be defined as endogenous (intrinsic) rhythmic changes occurring in an organism with a periodicity of approximately 24 hours. The rhythm will even persist for some days in the experimental absence of the daily rhythm of environmental cycles (e.g. light/dark) to which diurnal rhythm is usually entrained. In animals, diurnal rhythm is seen as sleep rhythms and running activity. Rhythms of hormone secretion have been implicated in some circadian rhythms but their existence implies some form of biological clock whose detailed biochemistry remains unknown. In methods according to the present invention, the administration of exogenous gonadotropins is towards the end of the animal's daily diurnal rhythm, i.e. it may be in the second half of the diurnal rhythm, preferably in the third quarter of the diurnal rhythm or in the fourth quarter of the diurnal rhythm. Assuming a general periodicity in the animal's diurnal rhythm of 24 hours, these periods are respectively, 12.00 am to 12.00 pm, 12.00 am to 6.00 pm and 6.00 pm to 12.00 pm local standard time.

Local standard time is defined as being the official time zone in the international time zone system at the place where the method is carried out. References in the present application to specific times should be interpreted as referring to the local standard time applying at the place where the method is carried out. Appropriate adjustments will of course need to be made to such times where different time systems are used, such as for example, during the winter months as opposed to the summer months.

In embodiments of the invention relating to compositions of oocytes, the oocytes substantially comprise oocytes prepared according to a defined method of the invention. Typically, such an oocyte population will comprise at least about 25% oocytes prepared according to a defined method of the invention. However, it will be understood that the overall developmental competence of the oocytes will increase as the proportion of the oocytes prepared according to a defined method of the invention increases. Thus, in a particular embodiment, an oocyte composition may comprise at least about 50%, at least about 75%, at least about 90%, or at least about 95% of oocytes prepared according to a defined method of the invention may be utilised. The term "substantially comprises" with reference to such oocyte compositions encompasses such preparations.

2. In vitro Maturation

Porcine oocytes can be harvested by any suitable means in the art for subsequent in vitro maturation. For example, oocytes can be obtained by surgical procedures, including laparotomy, carried out on animals under anaesthesia. The procedures can be carried out on live animals, although it is possible to collect oocytes from the ovaries of recently slaughtered animals post mortem. The selection of oocytes from the ovaries is carried out manually from follicles which are about from 3–8 mm in size are selected. In practice, a cumulus oocyte complex (COC) is aspirated from a follicle and the COC is subsequently matured in vitro. The matured oocytes are denuded of cumulus cells prior to use, i.e. the cumulus cells are removed. References to oocytes include COCs, where appropriate, and also vice versa.

The improved developmental competence of oocytes selected by a method in accordance with this aspect of the invention, is provided by culturing a harvested oocyte in vitro for between about 36 to about 48 hours. The time period is measured with reference to the time of transfer of isolated cumulus oocyte complexes into culture medium containing gonadotropin hormone(s). The culture period may be from about 36 to about 48 hours, suitably from about 42 to 46 hours and preferably from about 43 to about 45 hours. The culture may be carried out in any suitable in vitro maturation medium, e.g. according to Wang et al (*J. Reprod. Fertil.* 111 101–108 (1997)). Selection of an oocyte matured under these conditions (or a population of oocytes) provides an oocyte which has an improved competence for development compared to a control oocyte.

3. In vivo Maturation

The porcine oocyte may be harvested by any suitable means in the art. For example, oocytes can be obtained by surgical procedures, including laparotomy, carried out on animals under anaesthesia. Alternative procedures include the use of media to flush out oocytes from the fallopian tubes. Suitably such procedures are carried out on live animals.

The improved developmental competence of oocytes selected by a method in accordance with this aspect of the invention, is provided by harvesting an oocyte from a pig from at about 42 to about 50 hours post injection with a gonadotropin hormone, wherein the oocyte is ovulated from about 42 to 50 hours post-gonadotropin injection. The time period can be measured with reference to the time of injection of the animal with a gonadotropin hormone to induce superovulation where transcutaneous ultrasonography is used to confirm that ovulation has occurred. Suitable gonadotropin hormone preparations are known in the art and include, but are not limited to, Pregnant Mares Serum Gonadotropin (PMSG), human chorionic gonadotropin (hCG), equine Chorionic Gonadotropin (eCG) or Gonadotropin Releasing Hormone (GnRH). While oocytes harvested within the 42–50 hour post-gonadotropin period show enhanced developmental competence, greater developmental competence may be obtained by harvesting oocytes at from about 44 to 48 hours or from about 45 to about 47 hours. Selection of an oocyte ovulated under these conditions (or a population of oocytes) provides an oocyte which has an improved competence for development.

The present application will find great utility in controlled super-ovulation in animals. Generally, this procedure involves at least one injection of a gonadotropin hormone to the animal from which oocytes are to be collected. Preferably, the procedure involves the administration of a first injection and a second injection which are separated by about three to four days, for example three and a half days. The two injections can be separated by about 72 to 96 hours, suitably about 78 to 92 hours, more preferably separated by about 83 to 88 hours, in which the first injection is administered towards the end of the diurnal rhythm of the animal as described above.

Using local standard time as a base from which to calculate the times for administration of the injections, it can be seen that the first injection should preferably be made during the second half of the diurnal rhythm of the animal, i.e. in the afternoon or early evening. Generally, the first injection can be given between 6.00 pm to 8.00 pm local standard time, preferably at 7.00 pm local standard time. The second injection can then be given subsequently allowing for the separation as described above. The second injection can therefore be given at 10.00 am to 12.00 am local standard time, preferably at 11.00 am local standard time, where the separation is 88 hours between the first and second injection. However, the skilled person will be able to determine other injection time protocols with reference to the parameters already outlined.

In a preferred embodiment of the invention, the gonadotropin hormone administered in the first injection can be Pregnant Mares Serum Gonadotropin (PMSG). In a further preferred embodiment of the invention, the gonadotropin hormone administered in the second injection can be human chorionic gonadotropin (hCG) or Gonadotropin Releasing Hormone (GnRH). The gonadotropin may administered in combination with other hormones, for example steroid hormones, such as a prostaglandin, including synthetic prostaglandins e.g. cloprostinol.

The injection of PMSG is generally understood to be responsible for recruitment of follicles which contain the oocytes to be ovulated. The second injection of a gonadotropin hormone such as hCG, induces ovulation and maturation of the oocyte.

Ovulation in an animal can be defined to have occurred when the majority of follicles surrounding an oocyte have disappeared as seen using transcutaneous ultrasonography. Methods practised in accordance with the present invention can therefore involve, but are not limited to, the use of transcutaneous ultrasonography to evaluate precisely and non-invasively the timing of ovulation. Such monitoring of the time of ovulation permits selection of oocytes for collection which have undergone a delayed ovulation as a result of the superovulation protocol used as described above. Monitoring the time of ovulation is valuable as it enables the determination of the developmental competence of an oocyte by selection according to a method of this aspect of the present invention. In order to achieve the full advantages of this aspect of the present invention, the time of ovulation should be known.

4. Applications of the Invention

Currently, mature oocytes are utilised in a number of technical procedures, including nuclear transfer and methods of in vitro production (IVP) of animals, such as in vitro fertilization (IVF). The oocytes and oocyte populations having optimal developmental competence prepared by the methods of the present invention may be used in these and other procedures and applications.

(a) Application of Invention in Methods of Nuclear Transfer

In the method of this aspect of the invention described above, a nucleus is transferred from a donor cell to a recipient porcine oocyte prepared and matured as described herein. The use of this method is not restricted to a particular donor cell type. The donor cell may be as described in Wilmut et al *Nature* 385 810 (1997); Campbell et al *Nature* 380 64–66 (1996); or Cibelli et al *Science* 280 1256–1258 (1998). All cells of normal karyotype, including embryonic, foetal and adult somatic cells which can be used successfully in nuclear transfer may in principle be employed in a method according to the present invention. Foetal fibroblasts are a particularly useful class of donor cells. Generally suitable methods of nuclear transfer are described in Campbell et al *Theriogenology* 43 181 (1995), Collas et al *Mol. Reprod. Dev.* 38 264–267 (1994), Keefer et al *Biol. Reprod.* 50 935–939 (1994), Sims et al *Proc. Nat'l. Acad. Sci. USA* 90 6143–6147 (1993), WO-A-9426884, WO-A-9424274, WO-A-9807841, WO-A-9003432, U.S. Pat. No. 4,994,384 and U.S. Pat. No. 5,057,420. The invention therefore contemplates the use of an at least partially differentiated cell, including a fully differentiated cell. Donor cells may be, but do not have to be, in culture and may be quiescent. Nuclear donor cells which are quiescent are cells which can be induced to enter quiescence or exist in a quiescent state in vivo.

The recipient cell into which the donor nucleus has been transferred may be cultured in vitro or in vivo until a suitable stage in embryonic development is reached. The invention includes the derivation of a cell line from desired cells of the embryo, e.g. inner cell mass cells, for example in the derivation of a stem cell line. Suitably, the embryo may be cultured to the blastocyst stage. This aspect of the invention therefore includes a cell, a cell line, or an embryo prepared according to a method as described above, and an animal prepared by allowing such an embryo to develop to term in the final recipient animal.

(b) Application of Invention in Methods of in vitro Production of Pigs

In vitro production can include any or all of the following three stages: (1) in vitro maturation (IVM) of the oocyte; (2) in vitro fertilization (IVF) of the oocyte; and/or (3) in vitro culture (IVC) of the fertilized oocyte, generally to the blastocyst stage. Generally, the oocyte to be fertilized will be subjected to in vitro maturation step prior to being brought into proximity with the sperm cell. In vitro production of an animal embryo will typically involve in vitro fertilization of animal oocytes and can be achieved by any suitable method depending upon the animal species. Examples of such methods include, but are not limited to those of Trounson et al *Theriogenology* 41 57–66 (1994); Thompson, J. G. *Reprod. Fertil. Dev.* 9 341–354 (1997); Wilmut et al in *Genetics of the Sheep*, pages 395–412 ed.s Piper, L. and Ruvinsky, A., CAB International, Oxford, UK (1997); Summers et al *Biol. Reprod.* 53 431–437 (1995); Weston, A. M. and Wolf, D. P. *Mol. Reprod. Dev.* 44 88–92 (1996); Liu et al *Mol. Reprod. Dev.* 45 157–162 (1996); Li et al *Theriogenology* 47 1103–1113 (1997); Trounson, A. and Gardner, D. K. ed.s *Handbook of in vitro Fertilisation*, CRC Press Inc. Salem, USA (1993)). This aspect of the invention may also involve in vitro culture of the resultant animal embryos. It will also be readily appreciated that a method according to this aspect of the invention may also include further screening steps for the viability of the embryo and its suitability for transfer to the final female recipient. Additionally, the method also extends to a cell or a cell line prepared from a porcine embryo according to a method of the invention.

(c) Application of Method to Transplantation Therapies

A pig prepared by a method in accordance with any aspect of the present invention may be used as a source of tissue for transplantation therapy. Similarly, a pig embryo prepared in this manner or a cell line developed therefrom may also be used in cell-transplantation therapy. Accordingly, there is provided in a further aspect of the invention a method of therapy comprising the administration of porcine cells to a patient, wherein the cells have been prepared from an embryo or animal prepared by a method as described above. This aspect of the invention extends to the use of such cells in medicine, e.g. cell-transplantation therapy, and also to the use of cells derived from such embryos in the preparation of a cell or tissue graft for transplantation. The cells may be organised into tissues, for example, heart, lung, liver, kidney, pancreas, corneas, nervous (e.g. brain, central nervous system, spinal cord), skin, or the cells may be blood cells (e.g. haemocytes, i.e. red blood cells, leucocytes) or haematopoietic stem cells or other stem cells (e.g. bone marrow). A method of the present invention will therefore also find utility in the preparation of xenografts. These methods might include in vitro differentiation of embryonic cells for therapeutic transplantation into a patient, including situations where the cells are genetically modified to correct a medical defect. Such applications might include treatment of diseases such as diabetes, Parkinson's disease, motor neurone disease, multiple sclerosis, AIDS etc, or disease conditions characterised by a loss of function in the cells or an organ of an affected individual.

Preferred features for the second and subsequent aspects of the invention are as for the first aspect mutatis mutandis.

EXAMPLES

The invention will now be further described by way of reference to the following Examples and Figures which are provided for the purposes of illustration only and are not to be construed as being limiting on the invention. Reference is made to a number of Figures in which:

FIG. 1 shows results of initial experiment to monitor the response of gilts to superovulatory stimuli in two different regimes. In regime 1 (□), Pregnant Mares Serum Gonadotropin (PMSG)/Prostaglandin injection was given at 5.00 pm local standard time in the UK, followed by an injection of human chorionic gonadotropin (hCG) after 88 hours at 9.00 am local standard time in the UK. In regime 2 (■), Pregnant Mares Serum Gonadotropin (PMSG)/Prostaglandin injection was given at 7.00 pm local standard time in the UK, followed by an injection of human chorionic gonadotropin (hCG) after 88 hours at 11.00 am local standard time in the UK. For both regimes, the PMSG/Prostaglandin injection was given 88 hours prior to the hCG injection.

FIG. 3 shows parthenogenetic development to blastocyst of ovulated porcine oocytes following electrical activation with reference to the time of ovulation.

FIG. 4 shows parthenogenetic development to blastocyst of porcine oocytes matured in vitro following electrical activation with reference to the period of maturation in vitro.

Example 1

Figure 1:
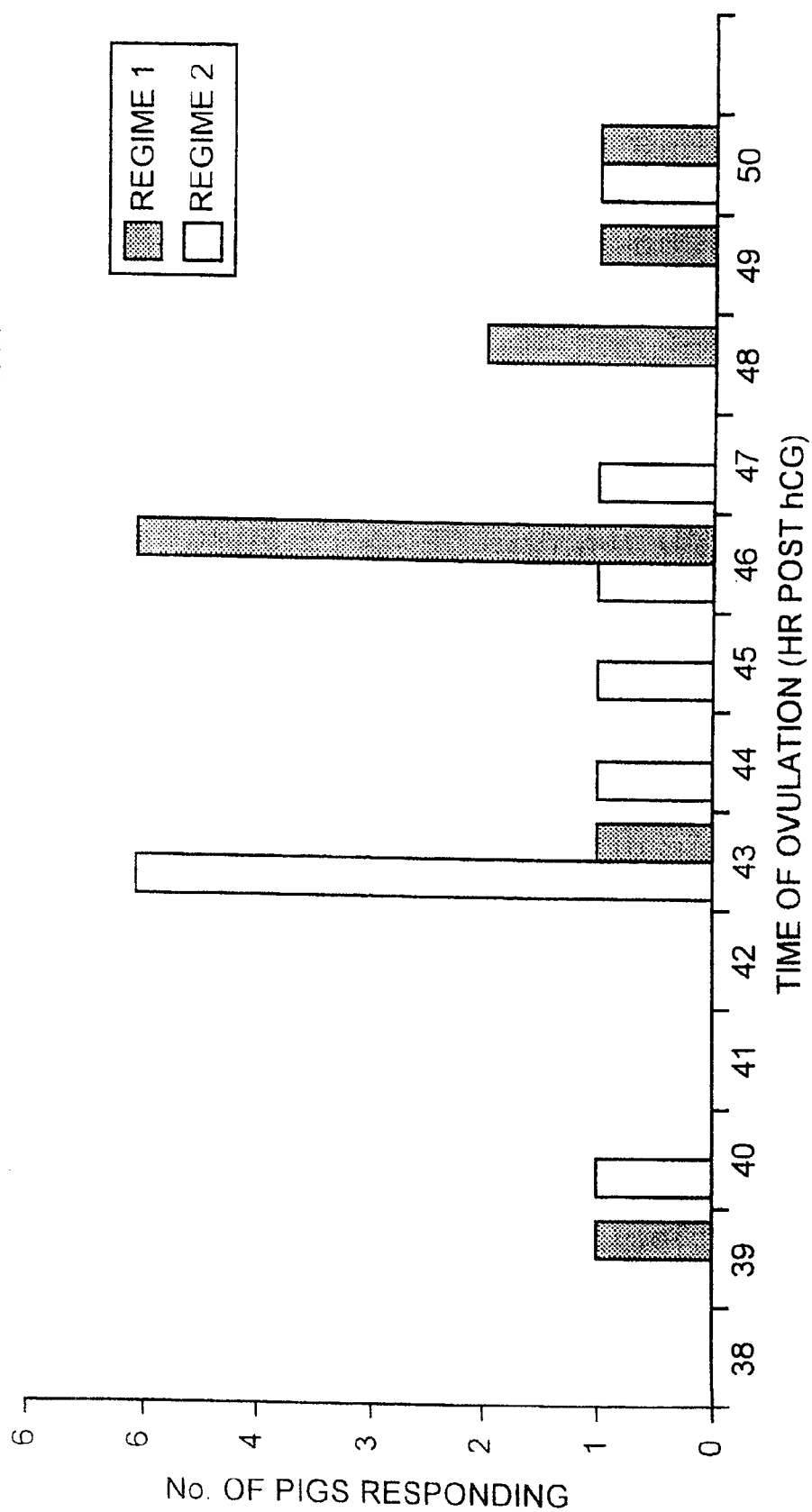

Developmental Competence of Oocytes Collected after Ovulation in vivo:

Synchronization of Oestrus and Superovulation

Cycling gilts were fed 5 mg of altrenogest daily for 18 days, which was followed by daily heat detection to establish a reference heat. Between 13–16 days after reference heat gilts were injected with 1500 IU of pregnant mares serum gonadotropin (PMSG) and 2 ml (175 µg) of cloprostinol (synthetic prostaglandin) at an appropriate time. Eighty-eight hours later this was followed with an injection of 500 IU of human chorionic gonadotropin (hCG). To delay the time of ovulation the timing of PMSG/hCG injections was shifted from the standard 5 pm (PMSG) and 9 am (hCG) by 2 hours to 7 pm (PMSG) and 11 am (hCG).

Detection of Ovulation

Ovulation was detected by transcutaneous ultrasonography using a real-time B-mode ultrasound machine with a 5 mhz convex linear probe. Scanning was carried out from 38 hours post hCG injection every 2 hours until 49 hours post-hCG injection. Ovulation was deemed to have occurred when the majority of the follicles had disappeared.

Collection of Oocytes

The oocytes were collected by performing a mid-line laparotomy on gilts under general anaesthesia. The reproductive tract was exposed, and following canulation the oviduct was flushed with collection medium (Calcium-free Hepes buffered M2 medium; Hogan et al in "Manipulating the Mouse Embryo: A Laboratory Manual", Cold Spring Harbour Laboratories, New York (1986)) prewarmed to 39° C. The collection medium may also be Hepes buffered M2 containing calcium or NCSU medium (Wang et al J. Reprod. Fertil. 111 101–108 (1997)), either with or without calcium.

Activation and Culture of Oocytes

Oocytes were activated electrically in 0.3M Mannitol, 100 µM $MgCl_2$, 50 µM $CaCl_2$, using 3 pulses of 80 µS duration at 1.25 kV/cm. This was followed by 3 washes in Hepes buffered MR2 medium and then culture for 5 hours in NCSU medium containing 1× BME Amino Acids (Sigma), 1× MEM non-essential amino acids (Sigma), 4 mg/ml Bovine Serum Albumen, 100 µg/ml cysteine and 7.5 µg/ml cytochalasin B at 39° C. in a 5% $O_2$, 5% $CO_2$, 90% $N_2$ environment (Abeydeera et al., Biol. Reprod. 58 213–218 (1998)). Activated oocytes were then washed free of and cultured in the same culture medium lacking cytochalasin B, in 20 µl microdrops under paraffin oil and the same gas atmosphere and temperature described above for 7 days.

Results

Figure 2:
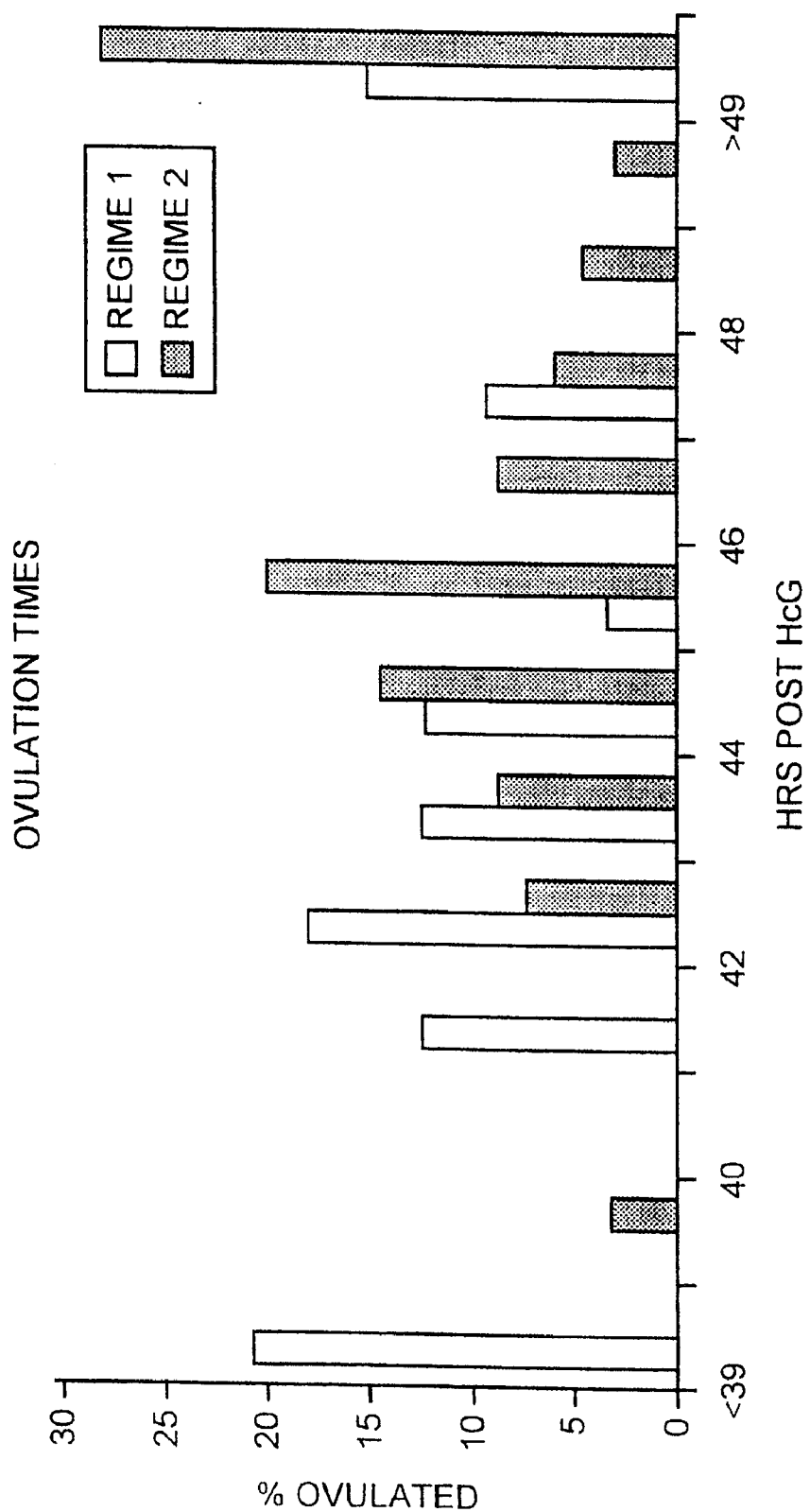
FIG. 2 shows results from expanded experiment to monitor the response of gilts to superovulatory stimuli in two different regimes as in FIG. 1.

The above methods were applied to mature gilts. In an initial set of experiments, 14 to 16 animals were allocated to each of two regimes wherein ovulation was induced by injection of PMSG and hCG. The regimes differed by a shift of 2 hours in the commencement of the protocol. This 2 hour shift resulted in a prolonging of the modal ovulation time by approximately 3 hours (see FIGS. 1 and 2). The development of parthenogenetically activated oocytes to the blastocyst stage was followed after 7 days of culture. Interestingly, the developmental competence of the oocytes correlated with the shift in modal ovulation time. A striking positive correlation was observed between the percentage of oocytes reaching the blastocyst stage (an endpoint of pre-attachment development) and the time with which those oocytes were ovulated (see FIG. 3). This trend demonstrates that oocytes which are ovulated later exhibit increased competence for embryonic development within a defined time period or window. The method described to prolong the onset of ovulation, which likely resulted from an interaction between the injected gonadotropins and diurnal variations in female responsiveness to these hormones, provides a means to improve the yield of developmentally competent oocytes for both natural and assisted reproductive strategies.

Example 2

Developmental Competence of Oocytes Matured in vitro

Collection of Oocytes

Ovaries were collected from a slaughterhouse into a thermal box containing gel pads pre-warmed to approximately 30° C. If the temperature of ovaries and pads is greater than 30° C. then pads are removed. During collection and transport, temperature of ovaries should be within 25–30° C. On arrival at the laboratory, ovaries were washed 2× with PBS and maintained in a beaker in a water bath at 25° C. during follicular aspiration. Cumulus oocyte complexes (COCs) were aspirated from 3–8 mm follicles using a 18 gauge needle attached to a 10 ml syringe and follicles were pierced from an interior surface. Aspirate is collected in sterile plastic universal vials. Needles should be temporarily removed when dispensing contents of syringe into vials. Aspirations should be completed within an hour of ovary arrival.

Collected COCs were washed 3× with TL-Hepes-PVA by draining all but one third of aspirate, and adding 5–10 mls of TL-Hepes-PVA (prewarmed to 39° C.). After allowing 1–2 minutes for COCs to settle during each wash, the process is repeated. Washed COCs were then sorted in sterile 60 mm dishes. Only COCs that are completely enclosed by non-expanded cumulus were selected. Dark, denuded oocytes were not selected. After selection COCs were washed through 3 further changes of TL-Hepes-PVA, followed by passage through 3×500 µl volumes of Maturation medium licking hormones in 4 well Nunc™ plate. Maturation medium consisted of 0.22 µm filter sterile, bicarbonate buffered North Carolina State University (NCSU23) medium (Wang et al (J. Reprod. Fertil. 111 101–108 (1997)) supplemented with 1× Basic Minimal Essential (BME; Sigma B-6766) and 1× Minimal Essential (MEM; Sigma M-7145) amino acids, and 10% pig follicular fluid.

In vitro Maturation

For maturation COCs were cultured for 22 hours in Maturation medium containing the hormones human Chorionic Gonadotropin (hCG) and Equine Chorionic Gonadotropin (eCG) to a final concentration of 10 IU/ml, respectively, followed by another 16 to 26 hours in maturation medium without hormones. All maturation was at 39° C. in a 5% $CO_2$ in air environment.

Activation

Prior to parthenogenetic activation oocytes were denuded of expanded cumulus by pipetting in Hepes buffered NCSU23 containing 600 IU/nl hyluronidase for 2 to 3 minutes at room temperature in groups of 50. Denuded oocytes were then washed in Calcium-free hbNCSU23 two times followed by passage through 2 volumes of activation medium (0.3M Mannitol, 50 µM $CaCl_2$, 100 µM $MgCl_2$). In groups of 25 washed oocytes were then loaded into an electrical activation chamber containing 200 µl of Mannitol over electrodes. Oocytes were aligned in single row, and were then subject to a pulse of 5 seconds×5V AC to further align them, followed by 3×80 μsec pulses of DC current at a field strength ranging from 1 to 1.5 KV/cm (preferably 1 KV/cm).

Electrically activated oocytes were next transferred into NCSU23 containing 7.5 μg/ml Cytochalasin B (or equivalent inhibitor of cytokinesis) for 6–8 hours at 39° C., 5% $CO_2$. After this treatment which is intended to suppress the emission of a second polar body, thus resulting in the creation of eggs which are karyotypically diploid, eggs were washed through 3 volumes of NCSU23 before finally being cultured in the same medium for up to 7 days at 39° C., 5% $CO_2$ in air.

Preparation of Pig Follicular Fluid for Archiving

After permitting follicular aspirate to settle in universal tube, top fluid was drawn off and centrifuged at room temperature for 30 minutes at 3000 rpm (1500 g). Supernatant was frozen as 1 ml aliquots at −20° C. Frozen aliquots can be used to prepare maturation medium in future experiments.

Studies on Activation Conditions for in vitro Matured Oocytes

Although 100% of in vitro matured pig oocytes can be activated parthenogenetically, the rate of blastocyst formation is still low. Experiments were carried out to investigate the best conditions for pig oocyte activation in order to improve its efficiency. In all experiments, pig oocyte maturation was undertaken according to a method described by Wang et al (*J. Reprod. Fertil.* 111 101–108 (1997)).

The timing of oocyte maturation in the in vitro maturation (IVM) system was studied as follows. Oocytes were fixed in acetic acid:methanol and stained by 1% orcein at 0, 22, 36, 37, 38, 39, 40, 41, 42 and 43 hours of maturation respectively to assess nuclear maturation. 82% of 50 oocytes arrested at GV stage at 0 h, 68% of 44 oocytes at MI stage at 22 hours, and 75% of 36 oocytes reached MII stage at 36 hours, after 37 hours and 43 hours more than 90% of oocytes were MII stage, confirming the efficiency of IVM.

Activation and Culture of Oocytes

The effects of different culture media and activation conditions were also investigated. In all experiments, activated oocytes were cultured in 7.5 μg/ml cytochalasin B for 6 hours, then transferred into NCSU23 medium+0.4% BSA and cultured for 6 or 7 days, at 39° C., in 5%$CO_2$ in air assess development to blastocyst stage.

(i) The effect of oocyte age and field strength were examined as follows. Oocytes were activated at 36, 40, 44 and 48 hours, with 1 pulse of 1.0, 1.25 and 1.5 kV/cm DC for 80 μs, respectively 0.3M Mannitol, 0.1 mM $Mg^2$, 0.05 mM $Ca^{2+}$ and were then cultured for 6 days. The results show that blastocyst rate increased from 36 to 44 hours of maturation in all the treatments (range from 14.5 to 41.1%), of which, the best result was 41.1% using 1 pulse of 1.5 kV/cm at 44 hours of maturation (see FIG. 4). Interestingly, at 48 hours the developmental competence of oocytes activated at virtually all electrical field strengths dropped. This demonstrates the existence of the limits of a window of developmental competence comparable to that seen in in vivo derived oocytes (see FIG. 3).

(ii) In this experiment pig oocytes matured for 44 hours were activated in the same medium as that in experiment (i) by combinations of 1, 3, 5 (×80 μs) pulse(s) of 1.0 kV/cm, 1.25 kV/cm and 1.5 kV/cm DC, respectively, following 0.25 kV/cm AC for 5 seconds. Blastocyst rate was significantly higher (54.3%) in the oocytes activated by 3 pulses of 1.0 kV/cm than those using other treatments (below 42.2%).

(iii) In this experiment, pig oocytes matured for 44 hours were activated in:

0.3M Mannitol alone (1),
0.3M Mannitol and 0.1 mM $Mg^{2+}$ (2),
0.3M Mannitol, 0.1 mM $Mg^{2+}$ and 0.05 mM $Ca^{2+}$ (3); and
0.3M Mannitol, 0.1 mM $Mg^{2+}$ and 0.1 mM $Ca^{2+}$ (4).

Activation was carried out using 3 pulses (×80 μs) of 1.0 k V/cm DC following 0.25 kV/cm AC for 5 seconds, followed by culture for 7 days. The medium (3) gave the best rate of blastocyst (44%) compared to the other media although the lowest rate was only 14.4% in the medium (2).

(iv) In this experiment, pig oocytes matured for 44 hours were activated in the medium (3), Sorbitol+0.1 mM $Mg^{2+}$+ 0.05 mM $Ca^{2+}$ and Zimmermann medium, respectively, by 3 pulses (×80 μs) of 1.25 kV/cm following 0.25 kV/cm AC for 5 seconds, the activated oocytes were then cultured for 7 days. No differences in blastocyst rate and mean cell numbers per blastocyst were observed among the three media (36.1%, N=374, 45.39+15.88 for medium 3, 35.4%, N=381, 51.70+20.72 for Sorbitol; and 40.62%, N=357, 46.12+21.14 for Zimmermann medium).

What is claimed is:

1. An improvement in the nuclear transfer method for cloning a pig, in which a pig oocyte is harvested from a donor animal and enucleated, the nucleus of a pig somatic cell is transferred into the enucleated oocyte to produce a combined cell, the combined cell is activated to produce an embryo, and the embryo is developed in a recipient animal of the same species to produce the cloned pig;

wherein the improvement comprises:
maturing the harvested oocyte by in vitro culture before enucleation and transfer of the pig somatic cell nucleus into the enucleated oocyte, and activating the combined cell, wherein the time from beginning maturation to activation is about 42–46 hours; thereby producing an embryo with an improved probability of developing into a cloned pig in the recipient animal.

2. The method of claim 1, wherein the oocyte is matured by culturing in a medium containing gonadotropic hormone and follicle stimulating hormone.

3. The method of claim 1, wherein the combined cell is activated by electrical stimulation.

4. The method of claim 1, wherein the nucleus is transferred from a quiescent cell.

5. The method of claim 1, in which the oocyte is cultured for about 42–46 hours as a cumulus oocyte complex.

6. An improvement in the nuclear transfer method for producing a non-human mammal, in which an oocyte is harvested from a donor mammal and enucleated, the nucleus of a somatic cell of the same species is transferred into the enucleated oocyte to produce a combined cell, the combined cell is activated to produce an embryo, and the embryo is developed in a recipient mammal of the same species to produce the mammal;

wherein the non-human mammal is a pig, and the improvement comprises:
maturing the harvested oocyte by in vitro culture before enucleation and transfer of the mammalian somatic cell nucleus into the enucleated oocyte, and activating the combined cell, wherein the time from beginning maturation to activation is about 43–45 hours; thereby producing an embryo with an improved probability of developing into a pig in the recipient mammal.

7. The method of claim 6, wherein the oocyte is matured by culturing in a medium containing gonadotropic hormone and follicle stimulating hormone.

8. The method of claim 6, which the cacyte is cultured for about 43–45 hours as a cumulus oocyte complex.

9. The method of claim 6, wherein the nucleus is transferred from a quiescent cell.

10. The method of claim 6, wherein the combined cell is activated by electrical stimulation.

* * * * *